United States Patent [19]
Schumaier

[11] Patent Number: 5,852,879
[45] Date of Patent: Dec. 29, 1998

[54] MOISTURE SENSITIVE ITEM DRYING APPLIANCE

[76] Inventor: Daniel R. Schumaier, Rte. 2, Elizabethton, Tenn. 37643

[21] Appl. No.: 848,502

[22] Filed: Apr. 28, 1997

Related U.S. Application Data

[63] Continuation-in-part of Ser. No. 427,804, Apr. 26, 1995, Pat. No. 5,640,783.
[51] Int. Cl.$^6$ ...................................................... F26B 19/00
[52] U.S. Cl. ................................... 34/80; 34/218; 34/225
[58] Field of Search .................................. 34/60, 74, 80, 34/202, 218, 224, 225, 275; 219/391, 399, 400

[56] References Cited

U.S. PATENT DOCUMENTS 4,764,351   8/1988   Hennebert et al. ..................... 422/292
5,546,678   8/1996   Dhaemers ............................... 34/275

*Primary Examiner*—Henry A. Bennett
*Assistant Examiner*—Steve Gravini

[57] ABSTRACT

A dryer appliance for demoisturizing a moisture sensitive item such as an electronic hearing aid, tooth brush, or the like, having a housing with a removable closure cap or door for providing a substantially sealed chamber and access thereto, a desiccant component mounted in the chamber, wall means substantially dividing the chamber into first and second regions, a support in the chamber for supporting at least one item within the first region, one or more passages interconnecting the first and second regions for providing a gas flow circulation path therethrough, gas moving and heater means mounted in the chamber, the circulation path of air in the chamber being such as to bring the air into recirculating contact with the gas moving and heater means and the item for a prescribed period of time to demoisturize the item.

46 Claims, 7 Drawing Sheets

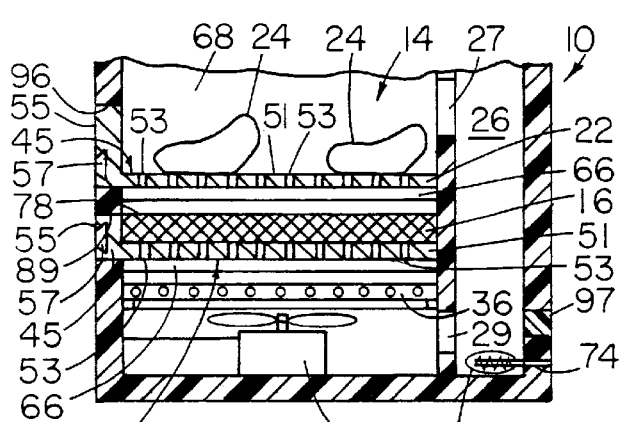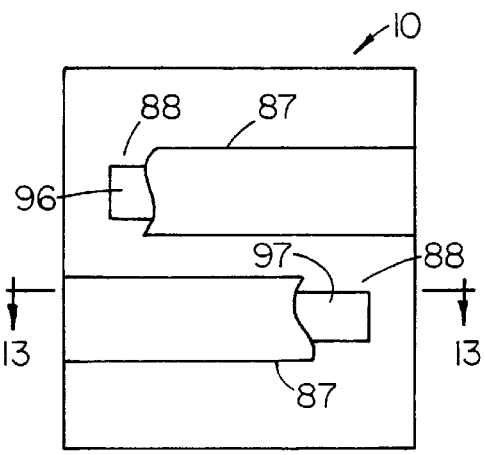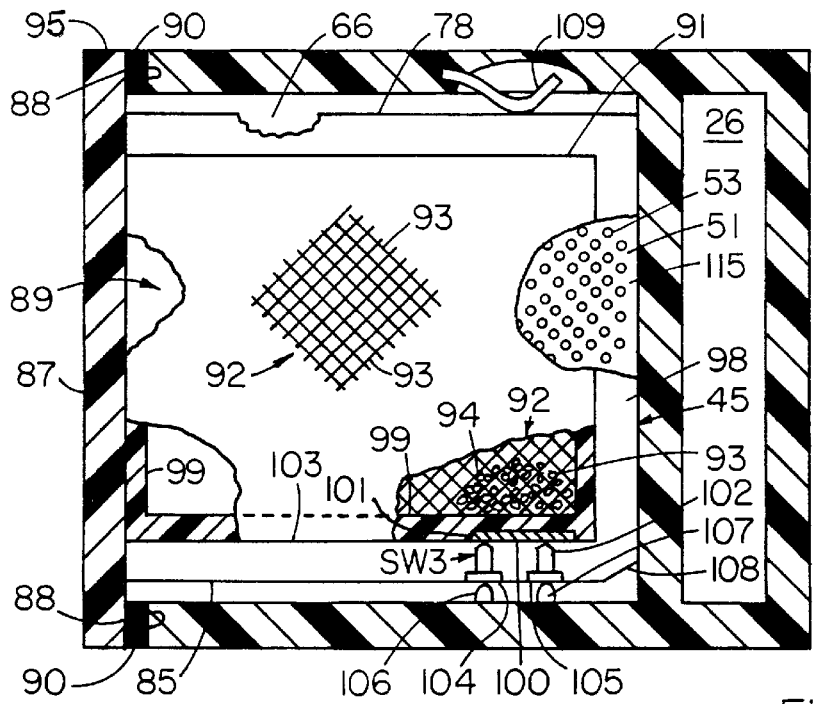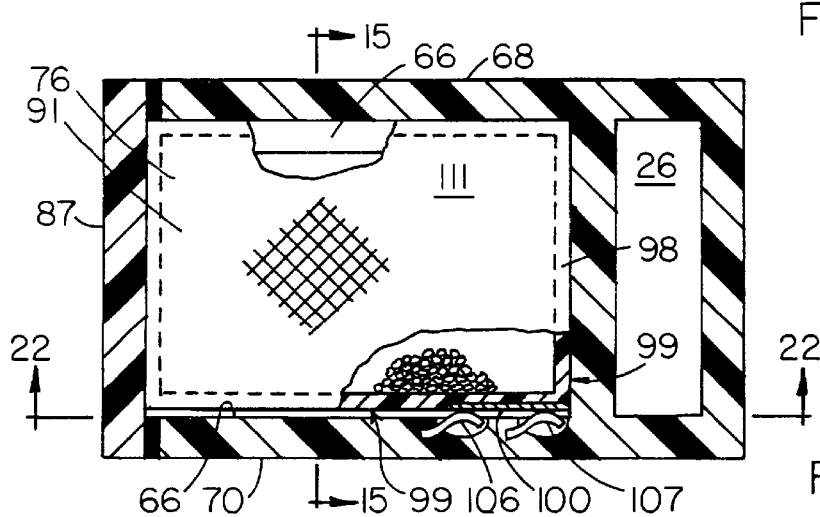

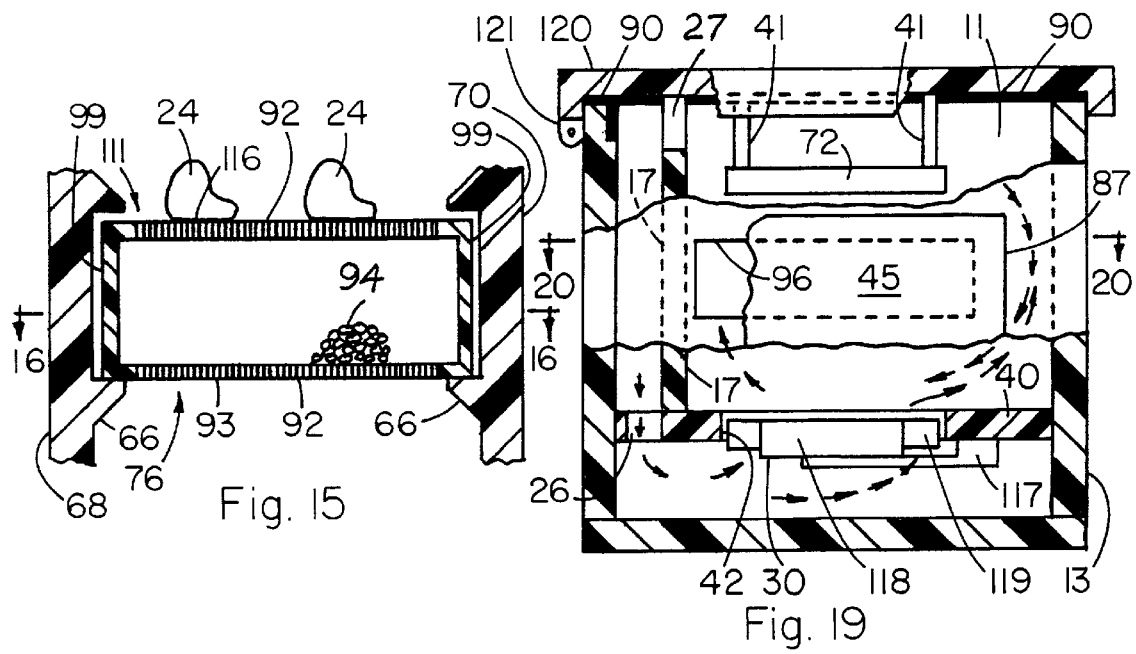
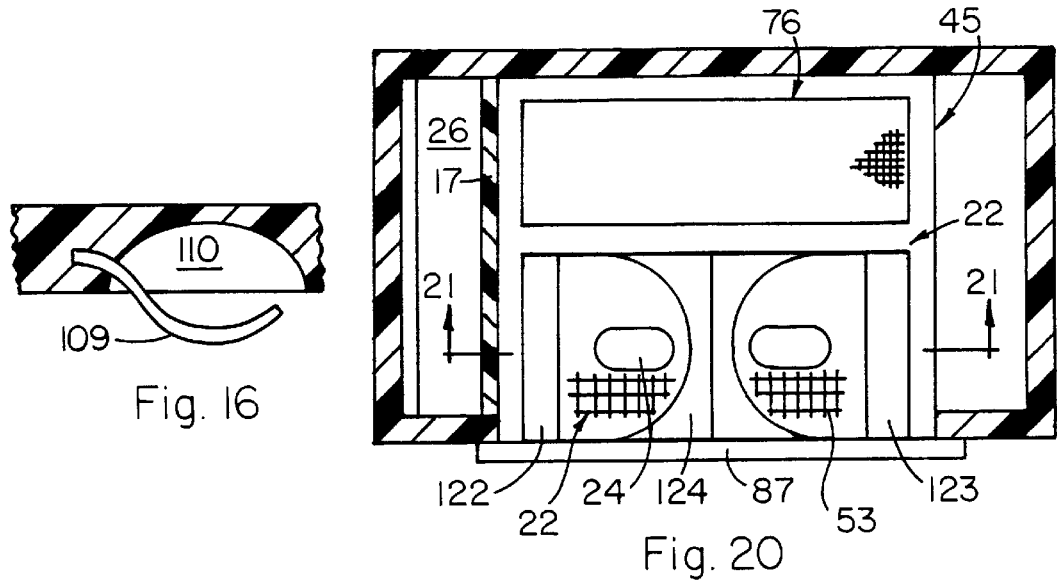
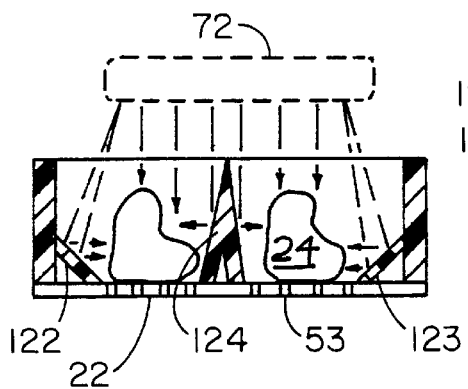
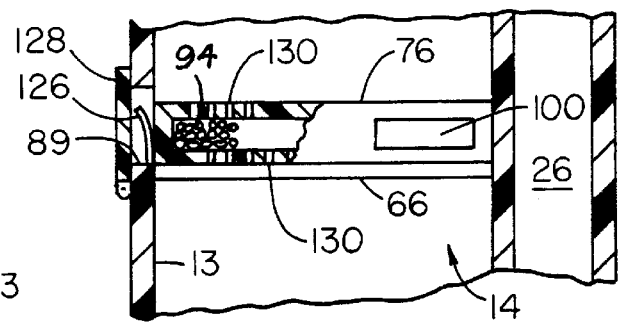

MOISTURE SENSITIVE ITEM DRYING APPLIANCE

This application is a continuation-in-part of Applicant's Ser. No. 08/427,804 filed Apr. 26, 1995, U.S. Pat. No. 5,640,783.

BACKGROUND OF THE INVENTION

1. Field of the Invention

This invention concerns a drying appliance for demoisturizing small items which come into contact with the human body, e.g., with body cavities such as ear canals, the mouth, or the like, and particularly concerns items which are sensitive to moisture or bacteria such as hearing aids, hearing aid or other batteries, custom molded ear plugs and hearing protectors, tooth brushes, medical devices or the like, and for storing such items in a substantially dry and sanitized environment, whereby the longevity of the item and its long term functionality are markedly enhanced, and/or its sterilization is effected. The invention particularly concerns such an appliance which is readily transportable, self-contained, and especially adapted for maintaining the operability and sterile condition of moisture or bacteria sensitive hearing aids and other small and intricate electrical or electronic devices.

It is a common characteristic of electrical or electronic devices or items, particularly where electrical or electronic switching components, or miniaturized batteries or the like are involved, for the circuitry to become corroded, short circuited, chemically attacked, or otherwise rendered less effective or completely inoperable by contact of the item with moisture, either from the ambient atmosphere, by structure damaging accident or, as in the case of hearing aids, from contact also with the user's moist body tissues and the bacteria or fungi carried thereon, and by ambient humidity which fosters, in particular, chemical activity and bacterial growth. Also, and of marked concern is the fact that external otitis (infection in the ear canal) is a common malady for hearing aid users. The insertion of a hearing aid or mold into the ear canal reduces the ability of air to circulate causing increased moisture in the canal and also produces ideal conditions for bacteria development. In this regard, many hearing air users utilize ear drops at night which dry the ear canal and tend to keep it acidic in order to prevent or reduce otitis. However, each day's insertion of a hearing aid can reintroduce old bacteria or earmold from the hearing aid back into the ear canal.

2. Description of the Prior Art

Heretofore, storage units for small electrical items such as button type batteries, and solar powered hearing aids have been developed as exemplified in U.S. Pat. Nos. 5,129,546; 5,210,804; and Des. 333,385. While these units are no doubt useful for their intended purposes, they do not address the moisture problems discussed above and are not capable of functioning in a truly effective demoisturizing manner.

OBJECTS OF THE INVENTION

Objects, therefore, of the present invention are: to provide an appliance means for demoisturizing moisture sensitive items, and for storing the same under dry conditions; to provide such appliance which is self-contained and easily transportable; to provide such appliance with structure which affords protection to the item against damage while not in use and which also affords a convenient and attractive storage facility therefor; to provide such appliance in a structural form which allows for easy assembly of the structural components thereof, and thus its maintenance; to provide such appliance with safety means comprising automatic electrical switching means activated by proper placement of essential components and items therein; and to provide such appliance in a miniaturized form whereby it can be easily carried in a handbag, small suitcase or the like.

SUMMARY OF THE INVENTION

These and other objects hereinafter becoming evident have been attained in accordance with the present invention through the discovery of certain structure for an appliance for demoisturizing moisture sensitive items, which structure, in its broad aspects, comprises housing means formed by wall means and adapted to provide substantially sealed chamber means containing a substantially singular quantity of gas, access port means formed thru said wall means and providing access to said chamber means, said wall means providing removable closure means for said port means for substantially sealing said port means to gas flow therethrough, support or carriage means in said chamber means for carrying at least one moisture sensitive item therein such as electronic hearing aids, toothbrushes, medicinal preparations and devices, and the like, and also for carrying desiccant means, regulating or control means for said gas in said chamber means for heating and maintaining a flow of said gas in a circulation path in said chamber means, said support means being positioned in said circulation path whereby the circulated gas will come into contact with said desiccant means and said item in said chamber means for heating said gas to a temperature which enhances evaporation of moisture from said item without damaging said item or said desiccant means.

In certain preferred embodiments:

(a) said support means comprises a first carriage means for carrying at least one said item, and further comprises a second carriage means for carrying said desiccant means, said desiccant means substantially divides said chamber means into first and second regions, passage means is provided interconnecting said first and second regions for providing a gas flow circulation path therethrough, said circulation path comprising (a) gas flow from said second region into contact with and through said desiccant means, (b) then into and thru said first region whereby said item is contacted with at least partially desiccated air, (c) then thru said passage means back into said second region, and (d) then again into contact with said desiccant means to continue said circulation;

(b) said gas moving means comprises fan means mounted upstream of said desiccant means, and wherein said heater means is mounted between said desiccant means and said fan means, said fan means, desiccant means and heater means all being within said circulation path;

(c) said desiccant means and its mounting provide a substantially closed path for passage of circulating heated gas into said first region;

(d) said first carriage means comprises flexible net means having a contact area of less than about 10% of the surface area of the portion of said item which is in contact with said contact area;

(e) said support means is laterally displaced from said passage means whereby a substantial amount of the circulating gas moves into close proximity to said item;

(f) said desiccant means is removably carried by said second carriage means such that it can be readily replaced when its desired desiccating capacity is depleted;

(g) locator means is provided on interior portions of said housing means for functioning in cooperation with said support means and control means to position the same within said housing means, (h) said support means is located within said first region for supporting both said item and said desiccant means therein in substantially the same horizontal plane;

(i) sterilizing or germicidal means such as ultraviolet generating lamp means or replaceable chemical means such as alcohol or antibiotic containing, slow release pads, or ejector means for atomizing or spraying germicidal or anti-fungal material into the air flow stream is provided within the circulation path;

(j) said support means is in the form of a drawer means which can be easily slid in or out of the chamber means through said port means thru said wall means of said housing means;

(k) said heater means also functions as said fan means by energizing the gas molecules to flow in an upward direction toward said first region of said chamber means;

(l) an electrical circuit means is provided for controlling operation of said heater means and said fan means, and a safety switch is provided in said circuit means, and a specially constructed drawer means is provided as said support means for carrying said desiccant means and/or said item, wherein said drawer means and/or said desiccant means has a closing means for said switch whereby said switch is closed only when said drawer means and/or said desiccant means is properly positioned within said chamber means whereby the appliance can then be electrically energized, e.g., by a manual on/off button; and (m) said support means comprises a drawer means provided with a first compartment for said item, and a second compartment for said desiccant means, and reflector means for UV radiation is positioned in said second compartment for focusing said radiation toward said item.

The present appliance provides an attractive storage space for hearing aids which are not in use, while providing a drying and sterilizing environment for reducing or eliminating moisture and, at the same time, sterilizing the hearing aid, against earmold or the like. The dry environment also dries cerumen (ear wax) which coats onto the item, thus making removal of the cerumen therefrom much easier. When a UV lamp is employed, the ozone produced acts as a deodorizer, while direct irradiation of the item directly kills bacteria or the like.

In a general embodiment, the present appliance consists of a closed chamber with a miniature fan circulating heated air which is passed directly over the hearing aids. Situated anywhere within the chamber is a desiccant which absorbs moisture, which desiccant is easily removed when saturated and may be dried at a higher temperature such as in an oven, and reused repeatedly in the appliance. The chamber also preferably contains a germicidal lamp which may be directed into the air flow circulation path or directly onto the hearing aid or other item, thereby sterilizing the surface of the item as well as the circulated air. The heating element preferably is controlled by a thermostat for maintaining a constant temperature ideal for drying. An on/off switch and an indicator lamp for all electrically operated components may also be included. A special drawer may be provided for convenient insertion and removal of the item and/or the desiccant.

BRIEF DESCRIPTION OF THE DRAWINGS

The invention will be further understood from the drawings herein of certain preferred embodiments, wherein the structures are not drawn to scale, and the following description thereof, wherein:

FIG. 11 is a view as in FIGS. 1 and 2 showing a variation in the carriages, i.e., a pull out drawer type carriage means for carrying either of the items or desiccant means;

FIG. 12 is a front view of the appliance employing separate drawers for the item and desiccant;

FIG. 13 is a cross-sectional view taken along line 13—13 of FIG. 12 with portions broken away for clarity and showing the desiccant drawer, i.e., the second carriage or support means, provided with electrical switching means for making or breaking one or more safety or other electrical circuits of the appliance;

FIG. 14 is a partially cross-sectional view similar to FIG. 13 of a unitary desiccant package and pull-out drawer means of the present invention;

FIG. 15 is a cross sectional view taken along the line 15—15 of FIG. 14;

FIG. 16 is an enlarged cross-sectional view taken along line 16—16 of FIG. 15 and showing the drawer biasing mechanism;

FIG. 19 is a partially cross-sectional view showing one preferred, single drawer arrangement of the appliance;

FIG. 20 is a cross-sectional view taken along line 20—20 of FIG. 19 and showing a specialized drawer arrangement for the item and desiccant and employing UV radiation focusing means;

FIG. 21 is a cross-sectional view of the drawer of FIG. 20 taken along line 21—21 of FIG. 20;

FIG. 22 is a cross-sectional view of a variation of the structure of FIG. 14 taken along line 22—22 thereof;

DESCRIPTION OF THE PREFERRED EMBODIMENTS

Figure 1:
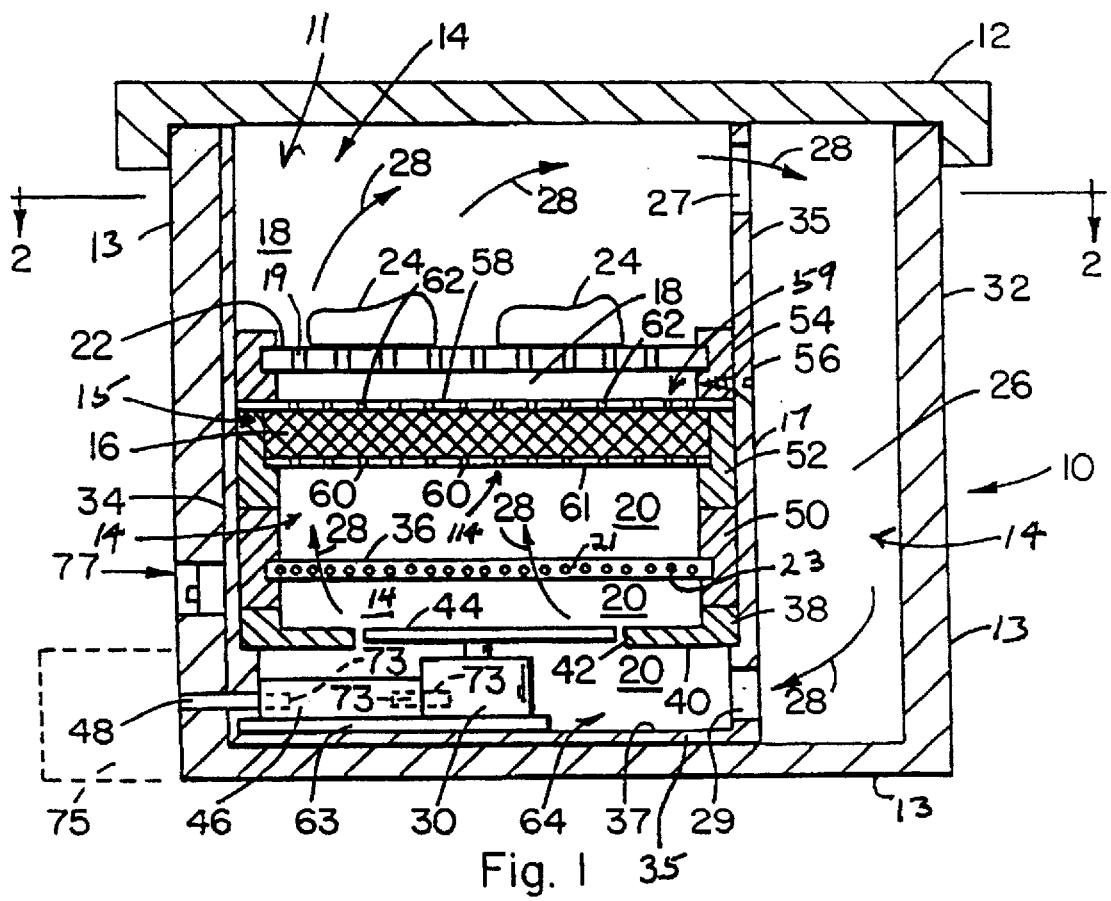
FIG. 1 is a longitudinal, vertical, cross-sectional view of the appliance.
Figure 2:
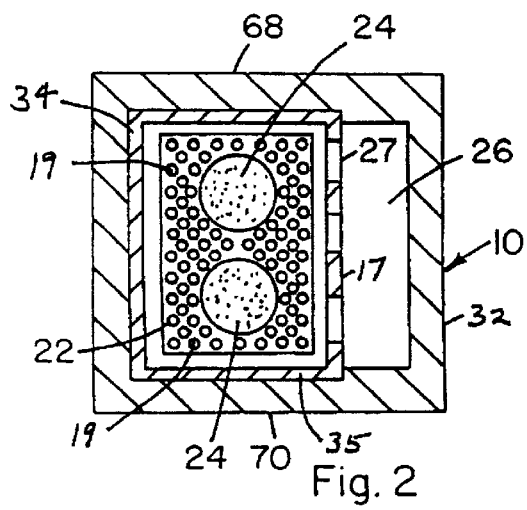
FIG. 2 is a lateral cross-sectional view taken along line 2—2 of FIG. 1 in the direction of the arrows.

Referring to the drawings, particularly FIGS. 1 and 2 and with particular reference to the claims hereof, the present appliance in one preferred embodiment comprises housing means generally designated 10 formed by wall means generally designated 13 having an access opening or port means 11 and a removable cap means 12 for providing substantially sealed chamber means generally designated 14 and access thereto, support means generally designated 15 comprising, in this particular embodiment, a first carriage means 22 for supporting an item, and a second carriage means 114 for a desiccant means, said desiccant means 16 comprising any moisture absorbing material such as supported granular CaO, $CaCl_2$, $ZnCl_2$, $CUSO_4$, silica gel or the like, panel means 17 mounted in said chamber means and forming a passage means 26 therein, said first and/or said second carriage means substantially dividing said chamber means 14 into first 18 and second 20 regions, openings 27 and 29 thru said panel means 17, which openings in combination with the plurality of aperture means 19 in first carriage means 22, and apertures 60 and 62 in second carriage means 114, interconnect said first and second regions for providing a gas flow, e.g., air flow circulation path generally designated 28 through said chamber means, said circulation path comprising (a) gas flow from said second region 20 into contact with and through said desiccant means 16, (b) then into said first region 18 for contact with said item, (c) then thru said passage means 26 back into said second region 20, and (d) then back into contact with said desiccant means 16 to continue said circulation path, and gas moving means 30 mounted in said chamber means 14 for forcing and maintaining said gas flow circulation path 28, and heater means 36 mounted in said chamber means for heating said gas.

Figure 6:
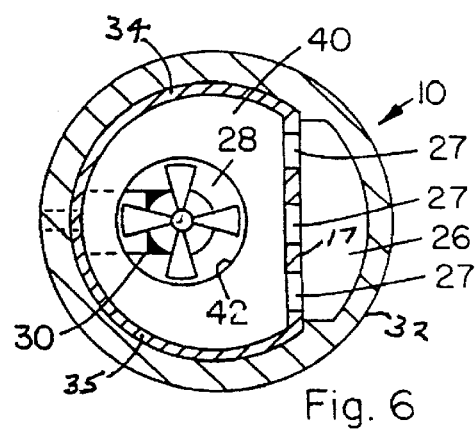
FIG. 6 is a view as in FIG. 2 with the item support, desiccant means, and heater means removed for clarity, and with the housing means configured generally circular in cross-section.

The housing means 10 can be of any configuration and material, for example, with a lateral cross-sectional shape of square, rectangular, oval or round, and of plastic, wood, ceramic or metal. As shown in FIGS. 1, 2 and 6, the housing may consist of an outer section 32 and an inner section 34 which, preferably, is in the general form of a removable cup 35. Mounted in the cup, or if only section 32 is employed, mounted on the inner wall portions and floor of the housing wall means 13, are the components 22, 16, 30, and heater 36 which heater preferably comprises a miniature electrical grid or resistance heater wherein the spacings 21 between the resistance wires 23 thereof allow air flow thru the heater to continue the circulation path 28.

Cap means 12 may be threaded onto the housing wall or dimensioned to provide a light friction fit which allows its removal by simple hand twisting and pulling force. This cap may be of any configuration and dimension such as and including the front piece 87 of the drawer type carriage means of FIGS. 13 and 14, and may be positioned anywhere on the housing. In this regard, a top access port may be eliminated in embodiments wherein the housing means is substantially permanently sealed and accesses to the aforesaid components is provided thru one or more access ports, e.g., thru a side of the housing wherein the components are supported on drawer means such as described below in regard to FIGS. 13 and 14.

In the construction shown in FIG. 1, the cup sides are provided with shoulder means 38 on which baffle plate 40 rests, said plate providing thru its circular opening 42 a portion of circulation path 28. The blade 44 of fan 30 preferably is mounted closely adjacent opening 42 such that its air moving efficiency is maximized and back flow wherein the desiccant means can be by-passed, is minimized.

In the embodiment of FIG. 11 which illustrates the drawer type support for the item and/or desiccant components of the appliance, a first port means 96 and a second port means 97 are formed thru the front wall of the housing for receiving first carriage means 22 and second carriage means 76 respectively. Each drawer 45, as illustrated for the first carriage means 22 and also for the second carriage means 76 comprises a floor means 51 having an adequate number of aperture means 53 therethrough for allowing proper drying air flow thru the carriage means. Each drawer preferably has a front piece 55 affixed to or integrally formed therewith and provided with handle means 57 such as a recess formed therein for being finger gripped for pulling the drawers out of the chamber. The floor means 51 is slidable on support rail means 66 affixed to each of the inner surfaces of opposite sides 68, 70 of the housing means and running from front to back of the housing.

Figure 18:
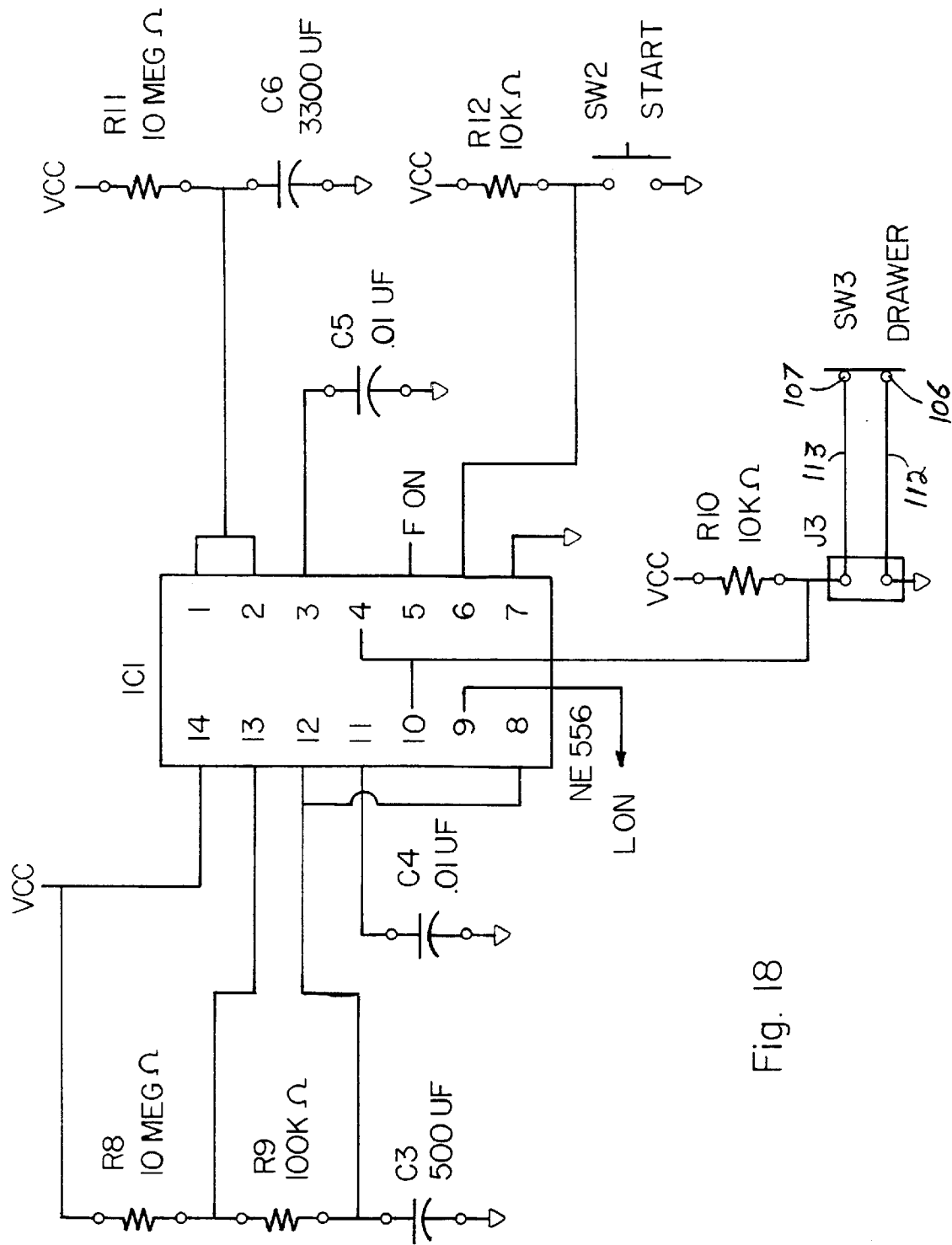

Referring to FIGS. 13 and 15, the drawer means 45 of this embodiment and comprising the second carriage means 76 can be constructed similarly to that of FIG. 11 and comprises the apertured floor means 51, side walls 78 and 85, rear wall 98 and a modified front piece 87. This front piece is adapted to substantially seal against facing portions 88 of the front of the housing means 10 when the drawer is pushed thru the rectangular second port means 89 in the front of the housing wall into the chamber to its operative position as shown in FIG. 13, i.e., the position where the operational safety requirements of the appliance are satisfied, and switch SW3 of FIG. 18 is closed. In this regard, sealing means 90 such as compressible polyurethane strip may be secured all the way around the peripheral portions 95 of the front piece to bear against the front facing portions 88 of the housing wall which define said port means and thereby assist in preventing the loss of desiccated air from chamber 14 during the drying and storage of the item, and thus preventing inopportune rehumidification of the item.

Referring further to FIG. 13, this particular embodiment of the desiccant means comprises a specially constructed package or packet 91, e.g., of from about 0.25 to about 1.5 inches in the thickness as shown in FIG. 15 and enclosed by a fine mesh, coarse fabric or plastic net material or the like 92 having openings 93 therethrough between the fibers or plastic strands or the like sufficient to readily allow air flow thru the loose or matrix block shaped granular or powder desiccant material 94 contained therein. While the packet is made somewhat cushionable in this embodiment such that it can be fairly tightly pushed down into the drawer cavity 115, it is preferred that the packet be provided with stiffening sides such as shown at 99 of plastic material such as, e.g., 20–30 mil thick sheet of polypropylene, cellulose ester, polyamide, or the like, such that the packet can be predimensioned to fit snugly against all sides or walls 78, 85, 98 of the drawer and remain so during its life, i.e., while it is still effective for the dehumidification.

In this regard, and with respect to providing the appliance with an electrical safety mechanism, and referring further to FIGS. 13 and 18, safety switch SW3 comprises, in one embodiment, a metal contact strip 100 which is also termed herein as a switch closure means, is adhesively or otherwise affixed to any surface portion of the desiccant packet, preferably to a side thereof as shown as 99. A pair of electrical contacts 101 and 102 are mounted thru a side such as 85 of the drawer and extend a short distance beyond its inside surface 103 such that strip 100 will slide on the contacts but firmly make an electrical connection between the contacts as the packet is placed into its operative position in the drawer as shown in FIG. 13. With the electrical connection thus made, the drawer can then be pushed into the housing thru the second port means 89 to the position shown in FIG. 13 such that the outer ends 104 and 105 of contacts 101 and 102 respectively make electrical contact with terminals 106 and 107 respectively as indicated in FIG. 13 to thereby place the electrical circuit in readiness. These terminals are electrically connected into the circuit of FIG. 18 by suitable leads 112, 113 shown in FIG. 18. In order to assist in proper drawer placement, the inner or rearward corner 108 of the drawer is beveled to allow it to readily slide over the terminals. In order to urge side wall 85 of the drawer and said contact ends 104 and 105 toward the terminals, one or more biasing means such as spring 109 mounted on the housing wall as shown in more detail in FIG. 16 may be employed. This spring, when flexed inwardly by the drawer wall can partially retreat into a cavity 110 in the housing wall as shown by dotted line in FIG. 16 and maintain a sufficient lateral force on the drawer to insure good contact of ends 104 and 105 with said terminals.

Referring to FIGS. 14 and 15, the desiccant packet and drawer means comprise a unitary desiccant unit generally designated 111 and is of the same general structure as packet 91 with equivalent structure numbered the same. This unit however, is preferably provided with somewhat more rigid structure than the packet 91 since the unit functions also as the second carriage means or drawer. To this end, the front wall of packet 111 may be affixed to the rigid front piece 87 by adhesive or the like, and the sides 99 and rear wall 98 of the packet are thickened, e.g., 0.125 in., and made fairly rigid such as to reduce lateral distortionability of the unit.

In this embodiment of FIG. 14, the biasing springs 109 are not employed to bias the drawer, but rather to serve as the terminals 106 and 107 such that a firm electrical connection between the contact strip or switch closure means 100 and said terminals is made and maintained when the desiccant packet is pushed inwardly thru port 89 to its operative position shown in FIG. 13. It is noted that equivalent switch devices can be placed at practically any position on either or both of said first or second carriage means and adjacent housing portions such that the electrical system of the appliance cannot be actuated, e.g., by a hand operated push button, toggle, or voltage change responsive touch type switch until both of said carriage means, or at least the desiccant means is in its operative position in chamber 14.

Referring further to FIG. 15, the concept is illustrated of employing the desiccant unit 111 also as the first carriage means whereby the items 24 may rest directly on the upper fabric surface 116 of the desiccant unit or on a highly porous fabric cushion or basket or the like, such as the radiation reflective cup means of FIGS. 23 and 24 hereinafter described in detail and positioned on said upper surface 116. In this embodiment the port means for the desiccant unit must be made of sufficient height dimensions as to allow the carriage means to slide in and out therethrough without causing contact of the items with the housing portions forming the top edge of the port means.

In all of the embodiments of the desiccant means described herein, and particularly those of FIGS. 13 and 14, the desiccant means itself may be provided with an indicator means such as a humidity sensitive patch located on a visible portion thereof which, e.g., undergoes a change in color, e.g., pink to blue as the desiccant material progressively looses its effectiveness. In this regard, it is preferred that said material be of a type and form which can be readily refurbished or regenerated by moderate heating, e.g., in a household oven for a period of, e.g., one or two hours. Such useful desiccants are market available as shown in the brochure entitled "MULTIFORM DESICCANTS", ®1996, of Multisorb Technologies, 325 Harlem Road, Buffalo, N.Y. 14224-1893, which brochure is hereby incorporated herein by reference.

In one particular embodiment wherein the appliance is to be used to sanitize special items which require treatment with special chemicals or other germicidal materials other than or in addition to UV radiation and dehumidification, a syringe needle penetrable gland element such as 97 of elastomeric material, or other closure structure, including a removable stopper means or the like, is provided in the housing wall at any location such that a hypodermic syringe or other ejector device can be used to spray, inject or atomize said materials into the gas flow stream.

Figure 17:
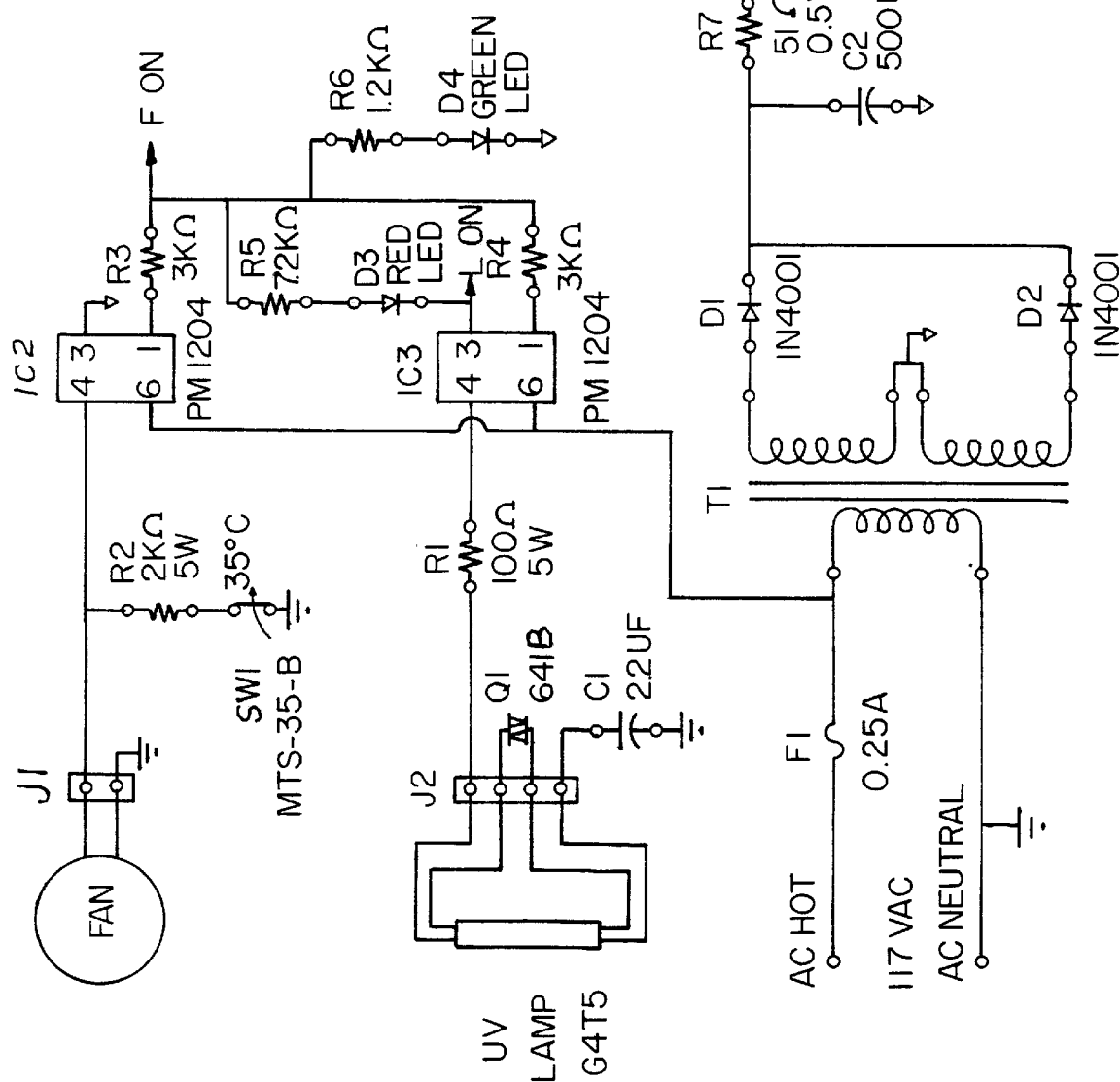
FIGS. 17 and 18 are electrical circuit schematics for controlling operations of the fan motor, the heater means, germicidal lamp means, and safety and indicator light means.

Referring to FIGS. 17 and 18, a preferred electronic circuit for operating the present appliance can be seen as four distinct sections: power supply, lamp driver, fan/heater and control components.

Power Supply:

The power supply is a 117 VAC to 15 VDC unregulated supply including components T1, D1, D2, C2 and R7. All portions of the circuitry have been protected via fuse F1.

Lamp Driver:

When activated, IC3 provides AC power. Components C1, Q1, R1 are used to both start and run a low power fluorescent lamp. The lamp is at a remote location and tied to the printed circuit board via connector J2.

Fan/Heater:

When activated, IC2 provides AC power for both the fan and the heating element R2. The heating element is used to quickly bring the dryer to, e.g., a 35 degree Celsius operating temperature. It is noted that this circuit can be adjusted to give any desired temperature range and any desired operating cycle or period to the heater and to the fan. When operating temperature is attained, thermal switch SW1 opens turning off the heating element. It for any reason the temperature drops below about 30 degrees Celsius or any other such desired low point, the heating element is reactivated. Since the fan is mounted remote, connector J1 is used to tie the fan to the printed circuit board. Preferably, the fan runs whenever the dryer is in operation.

Control:

ICI, a dual timer, provides timing functions for both IC2 and IC3, plus control of start and safety stop. Components R11, C6, C5 with ICI provide for the overall length of time the dryer is to be active. R3 and IC2, a solid state relay, provide isolation between the AC power and control circuits. They also provide power control for the fan/heater circuit. R6 and D4, a light emitting diode are used to indicate the dryer is functioning. This diode can be placed at any desired location within or on the housing such that it is readily visible to the user. Components R8, R9, C3 and C4 with ICI provide the on cycle and duration of the UV lamp. R4 and IC3, another solid state relay, provide isolation and control for the UV lamp circuit. R5 and D3 indicates when the UV lamp is lit. Components R12 and SW2 start the timing functions when SW2 is depressed. Components R12 and SW3 stop all functions and remove power from the UV lamp and fan if the dryer is opened. Switch SW3 is at a remote location and is tied to the printed circuit board using J3.

It is noted that such structural features as herein described are important to the preferred embodiments of the present invention in that the miniature sizes and powers of the components employed require conservative engineering in order to be efficient in the very limited spaces available for them. In this regard, a useful set of operating parameters for an electrically operated fan 30 and heater 36 are that the fan motor and the heater preferably can operate from either a permanent power source such as above described or from a three to six volt battery for about 30 minutes, with an airflow of from about 10 to about 50 cu.in./min., and a heat output of from about 0.5 to about 5.0 calories/min. Should such be desired, a solar panel device may be mounted on sun-exposed portions of the housing to generate sufficient electricity to recharge batteries or to directly power the fan and/or heater.

Such warmed, desiccated air-flow generally will satisfactorily dry a moist electronic item. Thereafter, the battery 46 can be recharged by any known and suitably reduced voltage power means thru, e.g., electrical prong and socket access port 48. The aforesaid operating parameters can, of course, be widely varied as also may the type and power consumption and output energies of the fan and heater and the voltage and operating life of their power supply. It is particularly noted that the type of heater which may be employed includes the chemical heater pack type which can be activated when desired and placed within the lower cavity 64. Such heating packs are typified by boot type warmers typically employing iron powder, water, vermiculite, activated charcoal and salts which, when exposed to oxygen within the contained package will chemically react and stay warm, e.g., about 100° F. for several hours. For such a heating means, access port 48 may comprise a laterally elongated slot provided with a suitable cover whereby the chemical pack can be inserted into and removed from cavity 64.

In the embodiment shown in FIG. 1, each component 36, 16, and 22 is provided with its own peripherally surrounding base means 50, 52 and 54 respectively which can be readily slid down into and stacked into cup 35. One or more screws such as 56 or other fastening means may be provided to fix base 54 to the cup side to thereby maintain the relative positions of all of the said components within the housing. It is noted that the support component 22 can actually be part of the top 58 of the desiccant means 16 within the scope of the terminology of the broad claims herein, in which case, screw 56 could be used alternatively in conjunction with base means 52. With such a stacking arrangement within cup 35, all of the components are rendered readily accessible for replacement or repair, e.g., replacement of the desiccant material simply by sliding the cup out of the outer section 32 of the housing, removing screw 56 and then lifting the components out of the cup. In this regard, the desiccant material is preferably carried in a module shell 59 comprising bottom plate 61 and top plate 58 having a sufficient number of inlet apertures 60 and outlet apertures 62 respectively to allow proper flow of recirculating air thru the desiccant.

Figure 7:
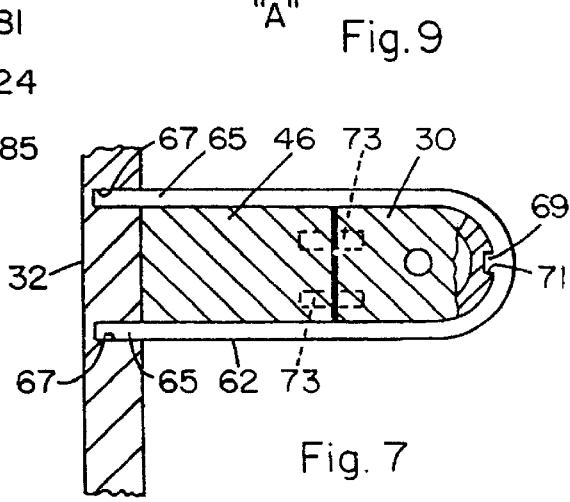
FIG. 7 is a view taken along line 7—7 of FIG. 1 in the direction of the arrows.
Figure 8:
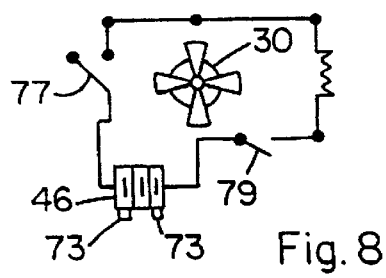
FIG. 8 is a schematic of an electrical circuit useful in the present appliance.

Referring to FIGS. 7 and 8, the battery 46 and motor 30 may be attached to each other in any suitable manner and affixed in position on the floor 37 of cup 35 by a strong and essentially inflexible bracket or clip 63, the ends 65 of which are pushed into tight fitting recesses 67 in the wall of section 32, and the nib 69 of which is inserted into recess 71 in the motor shell. With this construction, or with any equivalent construction, the motor and battery can be conveniently secured, but removably so, at a proper position in the appliance.

Figure 9:
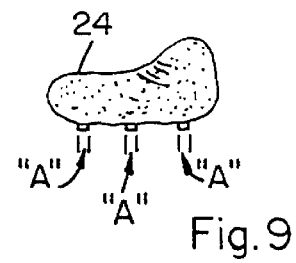
FIG. 9 is a side view of an item supported on a net, the cords of which are shown in cross-section in order to show the area "A" referred to herein.

A useful electrical circuit is shown schematically in FIG. 9 and in enlarged FIG. 8 wherein the connection of the battery to the motor, and of the battery to a charging unit 75 is made by plug in type connectors 73, and a push type, on/off switch 77 is mounted in wall 32, preferably flush with or inset from the outer surface of said wall for avoiding inopportune activation of the appliance during travel or the like. If desired, a second such switch 79 may be provided for the heater circuit such that the air circulation can proceed independently of heating the air. For extended periods of residency of the item in the appliance, this feature is very advantageous. It is noted that in situations where electrical power is available, the charging unit 75 and battery 30 may be replaced by a transformer device such that, e.g., normal house current may be used, in reduced voltage, to power the motor and heater. In this regard, the fan motor and electrical heater may be constructed to operate on house electrical power, e.g., 110 V, where, e.g., use of the appliance is to be only where such power is available.

The gas flow or circulation path 28 is initiated and maintained by gas moving means comprising either or both of fan 30 or heater 36. Where the residence time of the hearing aid in the appliance is, e.g., overnight, then the heater by itself will effect sufficient air flow upwardly thru the desiccant and cause sufficient air recirculation to subject the hearing aid to a continuously and sufficiently demoisturized gas flow to demoisturize the same. The obviously preferred gas is, of course air, however, for certain items which, e.g., may be prone to oxidation, a singular quantity, i.e., trapped amount of recirculating gas such as Helium may be injected by suitable means into the capped chamber and the air flushed therefrom and then resealed, whereby the Helium acts as the moisture pick-up medium.

A germicidal means such as a UV lamp 72 is preferably provided in any portion of the chamber means for purifying the recirculating air and the item. Suitable battery or house current electrical contact means 74 may extend through the housing wall for plug-in type, separate electrical connection. However, it is highly preferred that the lamp circuit be integrated into the overall appliance circuit such as shown in FIGS. 17 and 18. Such useful germicidal lamps and their specifications are described in the 16 page General Electric, Large Lamp Department publication, TP-122, October, 1970.

Figure 4:
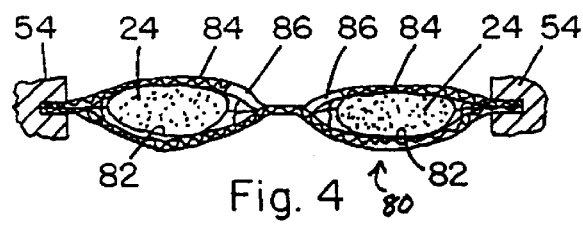
FIG. 4 is a cross-sectional view taken along line 4—4 of FIG. 3 in the direction of the arrows.
Figure 3:
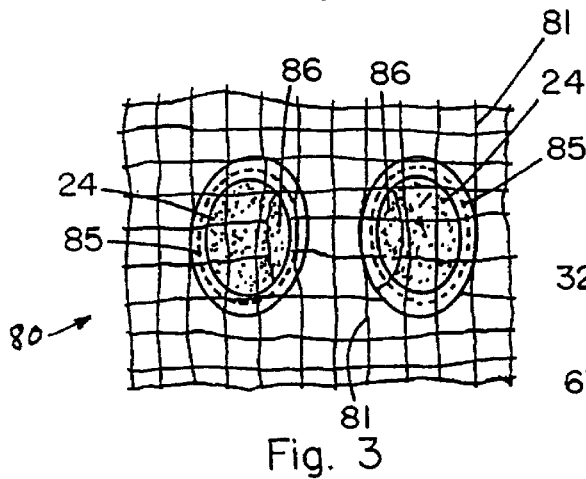
FIG. 3 is a top view of a preferred net form embodiment of the item support means.
Figure 5:
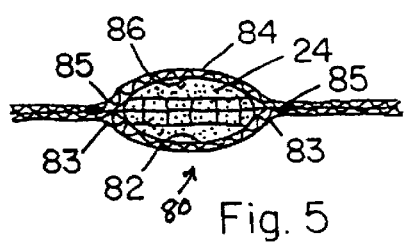
FIG. 5 is a view taken along line 5—5 of FIG. 4 in the direction of the arrows.

The net form construction 80 of the item support or carraige means as shown in FIGS. 3–5 may be of any natural or synthetic material, but preferably of fine denier cotton, silk, rayon or the like. This construction insures that the item will be essentially totally exposed to dry air flow since the netting covers only a minuscule surface area of the item. In this regard, such a small contact area, e.g., less than about 10% and preferably less than about 2% or less of the "total area" of the item surface which is substantially laterally covered by the cord 81 of the support means, and the nearly complete lack of mass of the netting cords, eliminates any formation of hot spots which might otherwise and damage the same.

The aforesaid total area is the aggregate of the areas "A" of the contacting cords which may be of dimensions and strengths such as that of heavy duty sewing thread. In a preferred form of the net, one or more pocket means generally designated 82 are formed therein, e.g., by stitching around the periphery of the pocket as at 83 or hot forming of, e.g., the polyester or Nylon thread, to receive the item, and preferably are provided with a cover portion 84 stitched or adhesively secured as at 85 around the pocket means and shaped to provide an access opening 86 through which the item can be passed. It is noted that the net type of construction for the pocket means 82 and cover portion 84 readily allows the netting to be flexibly expanded around the opening 86 for facilitating entry and removal of the item into and from the pocket and then closing slightly to secure the item therein. It is noted further that this net type of support provides considerable anti-shock safety for the item should the appliance be jostled about when being transported, or knocked from a night table, or the like.

Figure 10:
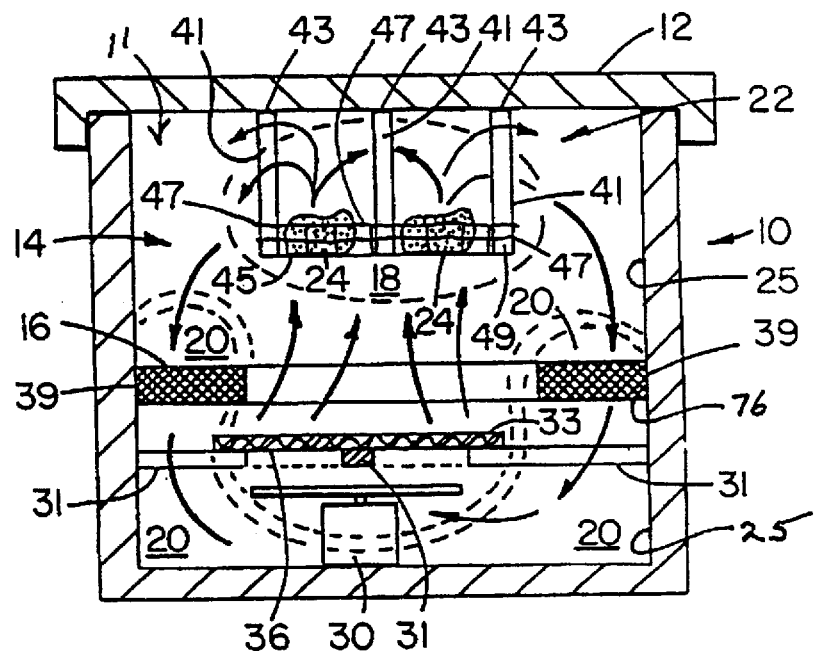
FIG. 10 is a cross-sectional view as in FIG. 1 showing an alternative arrangement of the various components of the appliance within the circulation path.

Referring to FIG. 10 wherein the identical or equivalent structures of FIG. 1 are numbered the same, the demoisturizing appliance comprises housing means 10 having removable cap means 12 for providing substantially sealed chamber means 14 and access thereto, desiccant means 16 mounted in said chamber means, support means 22 in a first region 18 in said chamber means for supporting at least one moisture sensitive item 24 therein, and gas moving means 30 in said chamber means for forcing and maintaining gas flow circulation in said chamber means and into contact with said desiccant means and said item, said circulation path comprising gas flow into contact with and through said desiccant means, then into and thru a first region 18 whereby said item is contacted with at least partially desiccated air, then into and thru a second region 20, and then again into contact with said desiccant means to continue said circulation.

In this embodiment, the grid heater 36, if a heater is to be employed, is supported by a plurality of members such as 31 which are secured at one end to the housing inner wall 25 and extend in a spider fashion radially inwardly to provide support end portions 33 for the heater. The desiccant means 16 may be of annular configuration with its radially outer periphery 39 affixed to wall 25, or the desiccant means may comprises, e.g., a plurality of arc-like segments affixed to wall 25. Referring to the embodiment of support means 22 of FIG. 10, a plurality, e.g., four circumferentially spaced hanger members 41 are affixed at their upper ends 43 to cap 12 and are secured at their lower ends 49 by adhesive or other means to a basket shaped net 45, the sides 47 of which extend upwardly a selected and sufficient distance to retain the items to the extent desired while allowing easy finger access thereto for entry into and removal from the support.

It is noted that region 18 is shown generally by dotted single outline, and region 20 is shown generally by dotted double outline. These regions are, of course, variable in scope, configuration, and location within said chamber means and within the context of the present invention, as are the particular locations and dimensions of the various components.

Referring to FIGS. 19–21 wherein structures equivalent to those previously described are numbered the same, the fan 30 is suspended in or under opening 42 in baffle plate 40 by means of one or more spider arms 117 affixed to the plate and the fan motor housing 118. These arms 117 are spaced apart circumferentially to allow plenty of space for the flow of gas upwardly thru the fan blades 119. In this embodiment, the UV lamp 72 is suspended from the inside of a hinged cover 120 such that when the cover is swung open around hinge means 121, the drawer or support means 45 for both the desiccant and items is fully exposed such that the items and desiccant can be easily installed or removed. The hinge means is preferably spring biased such that it continually urges the cover 120 to its closed position to ensure that the desiccant is protected against excessive atmospheric humidity due to unintentionally leaving the access port 11 open. Sealing cushion 90 secured either to the cover or housing wall assists in sealing port 11 and eliminates any thump should the cover 120 be allowed to spring closed.

In this embodiment, the desiccant packet and general structure of the drawer means, and the electrical contact circuitry may be as shown in FIG. 13. The item carriage portion of the drawer is preferably provided with reflective coated side sections 122, 123 and center section 124. These sections may be plastic sheet coated with aluminum, tin, or any other reflective material by adhesive means, metal vapor deposition, or the like. These sections assist in focusing extraneous UV radiation onto the item.

In FIG. 22, a variation of the desiccant carriage means 76 is provided with a pull-out tab 126 and a spring biased pull down door 128. The desiccant in this Figure is granular silica gel bound into a highly porous block shape by a shrink wrap of polyolefin having a large number of holes 130 therethrough for allowing easy passage of air thru the granular desiccant.

Figure 23:
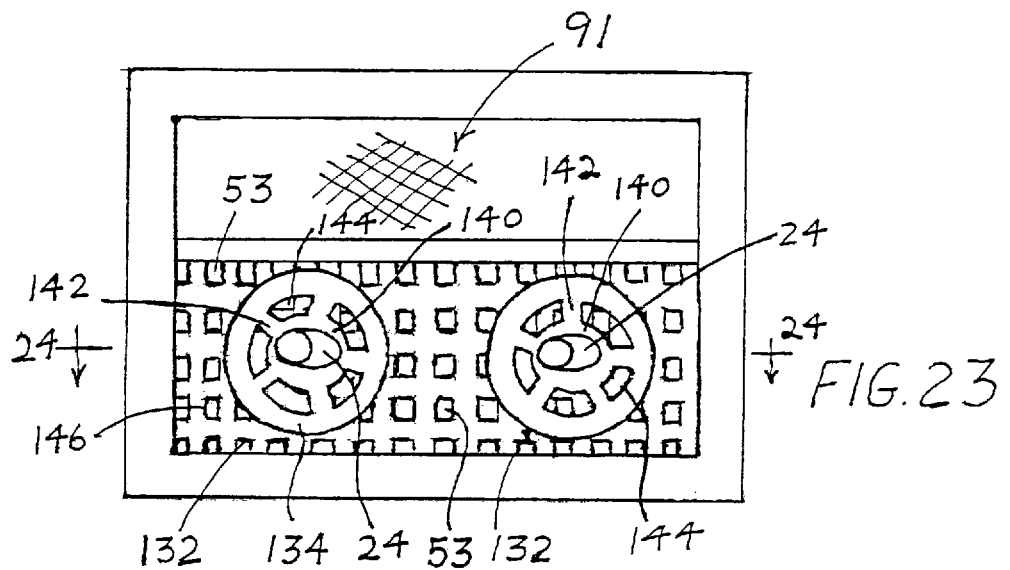
FIG. 23 is a top view of a variation of the item carriage means of the drawer of FIG. 20.
Figure 24:
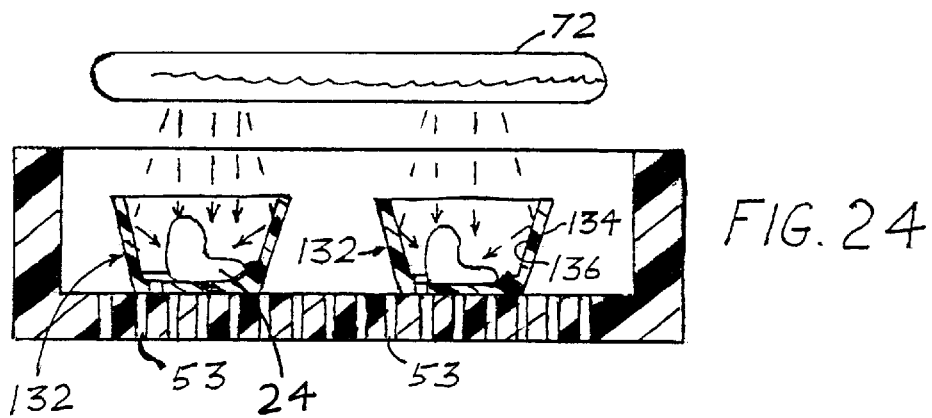
FIG. 24 is a cross-sectional view taken along line 24—24 of FIG. 23 with a UV lamp shown in dotted outline.

Referring to FIGS. 23 and 24, the radiation reflective means is shown as cup means 132 having a conical configuration with its side 134 coated with reflective metal or ceramic 136 on its inside surface. The bottom 138 of the cup may be configured with a tailor made pocket 140 for holding the item in any desired posture whereby the irradiation thereof is enhanced. Spider arms such as 142 connect side 134 and bottom 138 while providing sufficient spaces 144 for adequate gas flow to the items from between the carriage strands 146 or ribs.

The invention has been described in detail with particular reference to preferred embodiments thereof, but it will be understood that variations and modifications will be effected with the spirit and scope of the invention.

I claim:

1. An appliance for conditioning a moisture sensitive item such as an electronic hearing aid or the like, comprising housing means formed by wall means and providing substantially enclosed chamber means adapted to contain a substantially singular quantity of conditioner gas, said chamber means containing support means for carrying one or more items and a desiccant means, electrically operated control means for heating said gas and moving the same within said chamber means in a gas flow circulation path wherein the moving heated gas can substantially continuously contact said support means and an item and desiccant means carried thereby, whereby said item is exposed to drying conditions during a conditioning period, first port means thru said wall means for allowing said item to be placed within said chamber means or removed therefrom, electrial circuit means for energizing and de-energizing said control means, switch means in said circuit means, switch closing means on said support means for placing said circuit means in an operational condition when at least one said item and/or said desiccant means is placed in a predetermined position within said chamber means, and first removable closure means for substantially sealing said first port means against the passage of air therethrough.

2. The appliance of claim 1 wherein germicidal means is provided in said chamber means for sanitizing said item.

3. The appliance of claim 1 wherein said support means comprises first and second carriage means physically positioned within said chamber means and within a main gas flow stream of said circulation path.

4. The appliance of claim 3 wherein divider wall means is provided in said chamber means for directing the main gas flow stream into contact with said first and second carriage means and into contact with an item or desiccant means carried respectively thereon.

5. The appliance of claim 1 wherein said control means comprises an electrical resistance heater means and an electrically operated fan means.

6. The appliance of claim 5 wherein said heater means and fan means are structurally separated and each is positioned at any desired location within said chamber means.

7. The appliance of claim 4 wherein said divider wall means is provided within said chamber means and substantially divides said chamber means into first and second regions, said first carriage means being positioned in said first region and adapted to support at least one said item within said first region, passage means thru said divider wall means and interconnecting said first and second regions for providing a gas flow circulation path therethrough, wherein each circulation cycle brings the gas into contact with each of said first and second carriage means, and wherein germicidal UV lamp means is mounted in said chamber means for radiation sanitizing said item.

8. The appliance of claim 7 wherein said lamp means is mounted in said first region in close proximity to said first carriage means for directly irradiating a said item carried thereon.

9. The appliance of claim 7 wherein said control means comprises a fan means and a heater means, wherein said fan means is mounted upstream of said second carriage means, wherein said heater means is mounted between said second carriage means and said fan means, and wherein said fan means, second carriage means and heater means are all positioned within said circulation path.

10. The appliance of claim 2 wherein said germicidal means comprises ultraviolet radiation generating lamp means mounted in said chamber means in close proximity to said support means whereby the UV radiation is allowed to impinge directly on an item carried on said support means.

11. The appliance of claim 10 wherein said support means comprises first and second carriage means physically positioned within said chamber means and within a main gas flow stream of said circulation path, and wherein divider wall means is provided in said chamber means and substantially divides said chamber means into first and second regions, said first carriage means is adapted to support at least one said item within said first region, said divider wall means forms a passage means adapted to provide an intercommunication between said regions and provides for a gas flow circulation therebetween, said control means and second carriage means being mounted in said second region in upstream-to-downstream order whereby the circulation is thru a path comprising gas flow into contact with said control means and then into contact with said second carriage means, then into said first region for contact with an item on said first carriage means, and then back into said passage means and again into said second region.

12. The appliance of claim 7 wherein said first carriage means and desiccant means mounted thereon define a substantially confined path for passage of circulating gas from said second region into said first region whereby substantially all of said gas will pass thru the desiccant.

13. The appliance of claim 12 wherein said first carriage means comprises substantially rigid plate means having a plurality of apertures therethrough.

14. The appliance of claim 12 wherein said first carriage means comprises flexible net means.

15. The appliance of claim 1 wherein said support means is provided with surface means for engaging said item, said surface means having a contact area of less than about 10% of the area of said item which is in contact with said surface means.

16. The appliance of claim 15 wherein said support means is of flexible net construction.

17. The appliance of claim 16 wherein at least one pocket means is provided in said carriage means and adapted to receive and support an electronic hearing aid.

18. The appliance of claim 17 wherein said contact area is less than about 5% of the surface area of said hearing aid which is in contact with said carriage means.

19. The appliance of claim 7 wherein said first carriage means is laterally displaced from said passage means whereby substantially all of the circulating gas moves into close proximity to said item.

20. The appliance of claim 3 wherein either or both of said first and second carriage means comprises pull-out drawer means removably mounted thru first and second port means respectively thru said wall means of said housing means such that either drawer can be readily pulled out and exposed to the user by simple finger manipulation.

21. The appliance of claim 1 wherein said control means comprises a heater means and a fan means, and wherein mounting means for each of said fan means and heater means are provided in said housing and delimit the gas circulation path such that the gas must move essentially first through said fan means, then through said heater means on its way to said support means and the item supported thereby.

22. The appliance of claim 2 wherein said support means is affixed to an inner surface of cap means which is adapted to cover said first port means during said sanitizing.

23. The appliance of claim 22 wherein said support means comprises net means.

24. The appliance of claim 1 wherein said support means comprises net means.

25. The appliance of claim 24 wherein pocket means is formed in said net means for receiving said item.

26. The appliance of claim 7 wherein locator means is provided on interior portions of said wall means for functioning in cooperation with said control means, and said first and second carriage means to locate said control means and each said carriage means in operative position within said chamber means.

27. The appliance of claim 3 wherein said first carriage means comprises a surface portion of desiccant means mounted on said second carriage means.

28. The appliance of claim 27 wherein said desiccant means and said second carriage means comprises a single unit.

29. The appliance of claims 1 wherein said desiccant means and said support means comprises a single unit.

30. The appliance of claim 27 wherein said first and second carriage means and said desiccant means comprises a single unit.

31. The appliance of claim 18 wherein said pocket means is substantially closed and is provided with a substantially laterally oriented access opening for insertion and removal of said hearing aid.

32. The appliance of claim 1 wherein said control means comprises an electric resistance heater means which functions as and also comprises said gas moving means.

33. The appliance of claim 1 wherein UV lamp means is mounted in said chamber means over the top of said item support means such as to irradiate directly an item carried thereon.

34. The appliance of claim 21 wherein said fan means comprises a blade type fan mounted within said chamber means underneath said support means on support wall means which surrounds said fan in close proximity to the periphery of a blade means thereof, and wherein radiation reflective means is provided on the downstream side of said support wall means for reflecting toward said item from below at least a portion of the UV radiation which misses said item from above and passes thru or by said support means and impinges on said reflective means.

35. The appliance of claim 34 wherein said support means comprises a fibrous mesh material.

36. The appliance of claim 1 wherein wall means provided within said chamber means substantially divides said chamber means into and second regions, said first support means being adapted to support at least one said item within said first region, passage means thru said wall means and interconnecting said first and second regions for providing a gas flow circulation path therethrough, wherein a germicidal means is provided in said chamber means, wherein each circulation cycle brings the circulating gas into contact with said germicidal means and with any item carried by said first support means.

37. The appliance of claim 36 wherein said germicidal means is mounted within said gas flow circulation and comprises a slow-release, chemical composition.

38. The appliance of claim 37 wherein said germicidal means is provided in said chamber means as a released gaseous composition which becomes entrained with said gas flow and sanitizes the same and said item by molecular contact therewith.

39. The appliance of claim 1 wherein said first port means also serves as second port means for allowing desiccant means to be placed within said chamber means and removed therefrom.

40. The appliance of claim 39 wherein said support means comprises pull-out drawer means slidably mounted thru said first and second port means.

41. The appliance of claim 40 wherein a front portion of said drawer means provides a closure means for substantially sealing said first and second port means when said drawer means is operatively positioned within said chamber means.

42. The appliance of claim 40 wherein electrical circuit means is provided for energizing said control means, wherein said circuit contains a normally open switch means, wherein at least one of said drawer means or said desiccant means is provided with a closing means for said switch means, and wherein insertion of said drawer means thru said port means and to its operative position within said chamber means will cause said closing means to close said switch means.

43. The appliance of claim 42 wherein said desiccant means comprises moisture absorbing material contained within package means, and wherein said package means is provided with said closing means for said switch.

44. A desiccant package for use in a sanitizing appliance for moisture sensitive items, wherein the appliance has an electrical circuit means for controlling the operation of electrical components of the appliance, and wherein the circuit means is provided with normally open safety switch means, said package having switch closing means which is adapted to contact portions of said safety switch means to close said switch means upon operative placement of said package within said appliance.

45. The package of claim 44 wherein said switch closing means comprises electrical conductor means affixed to said package and adapted to contact and electrically interconnect positive and negative terminal means of said switch means.

46. The appliance of claim 1 wherein UV lamp means is provided in said chamber means in close proximity to said support means for irradiating an item carried on said support means, and radiation reflecting means is provided in said chamber means for directing radiation toward said item.

* * * * *